United States Patent [19]
Rahimi et al.

[11] Patent Number: 5,591,232
[45] Date of Patent: Jan. 7, 1997

[54] SURGICAL METHOD FOR REJUVENATING BODY MEMBERS OR FOR RESHAPING BODY MEMBERS OR FOR REJUVENATING AND RESHAPING BODY MEMBERS BY BONE GRAFTING

[76] Inventors: Houching Rahimi, 7550 Béique, Montreal, Québec, Canada, H4K 1A3; Hamid Vossoughi, 50 Watertown St. #609, Watertown, Mass. 02172

[21] Appl. No.: 422,812

[22] Filed: Apr. 17, 1995

[51] Int. Cl.⁶ .................................................... A61F 2/28
[52] U.S. Cl. .......................... 623/16; 128/898; 606/94; 606/86; 623/11
[58] Field of Search .................................. 623/11, 16, 18, 623/20; 606/86, 92, 93, 94; 128/898; 433/191, 195

[56] References Cited

U.S. PATENT DOCUMENTS

| | | | |
|---|---|---|---|
| 4,497,075 | 2/1985 | Niwa et al. | 606/76 |
| 4,725,234 | 2/1988 | Ethridge | 433/215 |
| 5,324,294 | 6/1994 | Elia et al. | 606/76 |

*Primary Examiner*—Robert A. H. Clarke
*Attorney, Agent, or Firm*—Weingarten, Schurgin, Gagnebin & Hayes LLP

[57] ABSTRACT

A surgical method for rejuvenating or reshaping body members which utilizes bone grafting. The method includes the steps of injecting physiological serum at a designated site of a body member; photographing the body member; determining the amount of serum which is equivalent to a quantity of bone graft mixture required for surgery; injecting the mixture at the designated site; and compacting and shaping the bone graft mixture and body member, respectively, until the desired shape is achieved.

16 Claims, No Drawings

SURGICAL METHOD FOR REJUVENATING BODY MEMBERS OR FOR RESHAPING BODY MEMBERS OR FOR REJUVENATING AND RESHAPING BODY MEMBERS BY BONE GRAFTING

BACKGROUND OF THE INVENTION

1. Field of the Invention

This invention relates to a new surgical method for rejuvenating body members or for reshaping body members or for rejuvenating and reshaping body members by using bone grafting, rather than lifting of skin or injection of components such as collagen. This new surgical method comprises:

(a) gradually injecting an amount of physiological serum at a designated site of a body member, comprising but not limited to a face;

(b) when a desired shape of the body member is achieved, photographing the body member, particularly the face, and determining the injected amount of physiological serum which is equivalent to a quantity of bone graft mixture (said "bone graft mixture" being a mixture of bone graft and hydroxylapatite) required for surgery;

(c) before injection, combining said bone graft mixture with normal saline, comprising approximately 0.9% by weight sodium chloride, to form a paste-like substance;

(d) making a number of incisions of few millimeters in oral epithelium or mucosa, and, from said number of incisions, making a tunnel to the designated site wherein the bone graft mixture is to be injected, insuring that no perforation occurs in the designated site of the bone graft mixture;

(e) removing any extra normal saline from the bone graft mixture;

(f) mixing the remaining bone graft mixture with few milliliters of fresh blood from the patient and injecting the desired quantity of bone graft mixture at the designated site; and (g) compacting the bone graft mixture gently in the designated site and closing said number of incisions by appropriate surgical sutures, while shaping the body member digitally by pressing on patient's outside skin until the desired shape of the body member is achieved.

2. General Background

The present invention relates to a new method for rejuvenating or a new method for reshaping a body member, as well as a combination of both methods, by using bone grafting. With age, more specifically around the age of forty, humans start loosing part of their bone mass throughout their body. The bones of the face are no exception to this natural phenomenon, which leads to collapse of facial skin and results in wrinkles.

Currently, surgeons rectify said collapse of skin, particularly facial skin, by lifting the skin or by injecting collagen and similar materials. Such a solution to the collapse of skin is thus limited to reshaping of soft tissues of the body member.

The purpose and novelty of the present method is a substitution, to the extent possible, of the lost bone mass by bone grafting. In order to use bone grafting for rejuvenation or reshaping, the present invention is recommended.

3. Description of the Prior Art

For many years, surgeons have been using different techniques as a means of rejuvenating or reshaping appearance of body members. One of such examples is use of face lifting techniques for rejuvenating and reshaping the face. A number of face lifting techniques have been developed in past several years. However, said number of face lifting techniques are usually relatively short-lasting. Due to aging, a need for having facial lifts speeds up rapidly. Some people have several facial lifts during their lifetime. Frequently complications result during and after performance of facial lifts. Substantial time may be required for achieving desired results during a lifetime. Some face lifting techniques may be relatively complicated and expensive. In addition, most of said face lifting techniques do not yield natural results because the appearance and expression of the face change with the facial lift. Thus, in a great number of cases, when the patient speaks or laughs, it becomes apparent that he or she has undergone facial lift.

In the past several years, there have been some tendencies to use bone grafting in several different areas of treatment. As an example, bone grafting has been used in "Alveolar Bone Grafting Process With Controlled Surface Active Ceramics", U.S. Pat. No. 4,725,234. In said patent, materials and dental procedures are disclosed for the treatment of resorbed or diseased periodontal and alveolar bone tissues. Biocompatible nonresorbable ceramic mixtures and compounds containing silicon, calcium, phosphorous, and sodium oxides and fluorides are prepared as powders or spheres and applied to defects or areas where it is desired to recontour the bone structure. This technique permits an improved method for corrective periodontal procedures and for alveolar ridge augmentation. However, the known prior art does not disclose the use of bone grafting as a rejuvenating or reshaping method as will be discussed.

SUMMARY OF THE INVENTION

A primary object of this invention is to provide a rejuvenation method by using bone grafting, rather than by skin lifts, silicon grafts or collagen injections.

A secondary object of this invention is to prevent bone loss in body members, such as nasal bones and cheek bones.

A tertiary object of this invention is to alter shapes of body members, comprising face or body bone structures, depending upon a patient's needs and desires.

Another object of this invention is to provide a rejuvenating method or a reshaping method or a combination of a rejuvenating method and a reshaping method that is relatively simple and easy to perform.

Another object of this invention is to provide a rejuvenating method or a reshaping method or a combination of both methods that is relatively inexpensive.

Still another object of this invention is to provide a rejuvenating method or a reshaping method or a combination of both methods that creates bone structure which is relatively long-lasting, stable and durable.

A further object of this invention is to provide a rejuvenating method or a reshaping method or a combination of both methods that requires a relatively short period of pre-surgical, surgical and post-surgical treatment.

Another object of the invention is to provide a rejuvenating method or a reshaping method or a combination of both methods where, particularly in upper and lower jaws and sub-orbital areas of patient's face, surgery is performed intra-orally, thus avoiding to the greatest extent possible external scars on the face of the patient or scars on patient's skin.

An additional object of the invention is to provide a rejuvenating method or a reshaping method or a combination of both methods that requires relatively simple and inexpensive chemicals and medical devices.

Another object of the invention is to provide a bone grafting method, comprising a rejuvenating method or a reshaping method or a combination of both methods, that, previous to the surgery, can estimate, predict and view resulting shape of a body member which is to be treated by bone grafting.

A further object of the invention is to provide a rejuvenating method or a reshaping method or a combination of both methods that permits realization of making a sculpture of a body member by taking an impression with alginate or other materials and adding wax on the sculpture to change said sculpture to a desired shape, said wax used to calculate an amount of bone graft mixture that is required.

Still another object of the invention is to provide a rejuvenating method or a reshaping method or a combination of both methods that may be performed, partially or totally, under local or general anesthesia, whichever is preferred.

A final object of the invention is to provide a facial rejuvenating or reshaping method whereby if, for any reason, the patient is not satisfied with final results, bone graft may be removed at any time after intervention, thus, making the final results reversible.

Additional objects and advantages of the invention will be set forth in part in a detailed description which follows, and in part will be obvious from the description, or may be learned by practice of the invention.

Said invention provides a new method for rejuvenating a body member or reshaping a body member or rejuvenating and reshaping a body member by using bone grafting, rather than lifting of skin or injecting components such as collagen. The new method for rejuvenating the body member or reshaping of the body member or rejuvenating and reshaping the body member comprises:

(a) gradually injecting an amount of physiological serum, including local anesthesia, at a designated site of the body member;

(b) when a desired shape of the body member is achieved, photographing the body member and determining the injected amount of physiological serum which is equivalent to a quantity of bone graft mixture required for surgery;

(c) before injection, combining said bone graft mixture with normal saline to form a paste-like bone graft mixture;

(d) making a number of incisions in oral mucosa from which a sub-periosteal tunnel is created to the designated site wherein the bone graft mixture is to be inserted, insuring that no perforation occurs in the designated site of the bone graft mixture, and through said tunnel transporting the paste-like bone graft mixture to the designated site;

(e) removing any extra normal saline from the paste-like bone graft mixture;

(f) mixing the remaining paste-like bone graft mixture with few milliliters of fresh blood from the patient and injecting the desired quantity of bone graft mixture at the designated site; and (g) compacting the bone graft mixture gently in the designated site and closing said number of incisions by appropriate surgical sutures, while shaping the body member digitally by pressing on patient's outside skin until the desired shape of the body member is achieved.

As can be seen, the rejuvenation method or the reshaping method or a combination of the rejuvenation method and the reshaping method is a relatively simple surgical procedure. It is also relatively economical, since it can be performed with a few inexpensive components in a relatively short time.

It is to be understood that the descriptions of this invention are exemplary and explanatory, but are not restrictive, of the invention. Other objects and advantages of this invention will become apparent from the following specification.

DETAILED DESCRIPTION OF THE PREFERRED EMBODIMENT

In a preferred embodiment, the present invention is a new method for partially or totally rejuvenating or reshaping or rejuvenating and reshaping a body member, comprising a face, hands and legs, by using bone grafting, rather than lifting skin or injecting components such as collagen. This new method for rejuvenation or reshaping of the body member or for a combination of rejuvenation and reshaping of the body member comprises several simple steps which may be performed in a short period of time by a surgeon. The first task is to determine whether a person would qualify as a candidate of surgery by bone grafting. All men and women with good general health and medical history are suitable candidates for treatment by bone grafting. However, surgery by bone grafting is not recommended for non-controlled diabetes patients. Special care must also be taken for patients with substantial traumatic or surgical scar on soft tissues.

If a person qualifies as a candidate, the next step is to determine quantity of bone graft needed. A few days before the surgery, the quantity of bone graft needed for surgical procedure is determined in a pre-surgical procedure. To determine the quantity of bone graft needed, a physiological serum, preferably including local anesthesia, is gradually injected as deep as possible at a location which is going to be a designated site of a bone graft mixture. In a preferred embodiment, the local anesthesia comprises lidocaine and epinephrin. The injected designated site is compared with a comparable non-injected site. For example, if the designated site is left cheek bone or left nasal bone, the injected left cheek bone is compared with the non-injected right cheek bone or the injected left nasal bone is compared with the non-injected right nasal bone, respectively. The physiological serum is added until a desired shape of the body member is obtained. The next step is to calculate the total amount of physiological serum that has been injected. The body member is then photographed when the desired shape of said body member is achieved. Thus, previous to the surgery, the resulting shape of the body member which is to be treated can be predicted and viewed.

The injected amount of physiological serum is equivalent to a quantity of the bone graft mixture that will be needed (before mixing any normal saline). Said bone graft mixture comprises from approximately 60 percent to approximately 80 percent by volume of bone graft and from approximately 20 percent to approximately 40 percent by volume of hydroxylapatite. The bone graft is derived from human or animal sources and is a freeze-dried, cortical bone powder. The hydroxylapatite component can be any kind of hydroxylapatite or Osteograf non-resorbable. Also, other types of bones or hydroxylapatites acceptable by Food and Drug Administration may be used. Use of corals is also recommended. Therefore, as can be seen, the rejuvenating method or the reshaping method or a combination of said methods may be provided relatively inexpensively.

An alternative solution to the above pre-surgical procedure is to make a plaster sculpture of the body member by taking an impression with alginate or other materials, and adding an amount of wax on the sculpture to achieve the desired shape. Calculations of the bone graft needed could then be made according to the amount of wax used. An advantage of said rejuvenating method or of said reshaping method or of the combination of both methods is that the patient is able to see the sculpture before commencing surgical treatment, if desired.

Currently, attempts are being made to find a computerized system that will determine the required quantity of bone graft and hydroxylapatite without requiring the preliminary injection or plaster sculpture. Such a computerized system would delete the need for the preliminary injection, while providing the patient with a picture of structure and shape of his or her body member after rejuvenating or reshaping surgery.

An amount of bone graft mixture equivalent to the amount of injected physiological serum consumed upon photographing is used during surgery. Proper rules and regulations of sterilization and infection control should be followed during the surgery and a written consent has to be signed by the patient. Appropriate antibiotics are given to the patient before and after the surgery. If the bone grafting surgery is for a large portion of the face, corticosteroids, pre-operatory and post-operatory, are required. Local or general anesthesia is given on a case-by-case basis depending upon needs of each patient. The bone graft mixture has to be prepared at least 30 minutes prior to injection, and mixed with an amount of normal saline. The preferred amount of normal saline is at least equal to volume of the bone graft mixture to insure that the bone graft powder particles absorb liquid that said particles need in order to become a paste-like substance.

More care should be taken for facial surgeries. For lower jaw or maxilla as well as molar and nasal areas, a number of periosteal incisions is made in oral mucosa. Then, a sub-periosteal tunnel is gently dissected to the designated site of the bone graft. Special care is taken to prevent any damages to mandibular and sub-orbital nerves, assuring that no perforation occurs in periosteum in the designated site of the bone graft. Before the injection of the bone graft mixture, any extra normal saline is removed and a few milliliters of fresh venous blood of the patient is added. Approximately 10 milliliters of fresh blood of the patient is preferred. The desired quantity of bone graft mixture is then transported through said tunnel to the designated site with the use of a special syringe or a special instrument. Thus, in upper and lower jaws and sub-orbital areas, the surgery may be performed intra-orally, avoiding external scars on patient's face or scars on patient's skin. For frontal and temporal parts, a number of incisions are made in external ends of eyebrows or in hair line. Said number of incisions are from skin to the periosteum, paying attention to supraorbital nerves.

The desired quantity of bone graft mixture is injected in the designated site. The bone graft mixture is then gently compacted in the designated site and the number of incisions are closed by appropriate surgical sutures. Meanwhile, the body member is shaped digitally by pressing on patient's outside skin until the desired shape is achieved. Post operative care, medication and instructions exist. On the average, weekly visits for approximately two months after surgery and removal of sutures are necessary. Any trauma or continued pressure on treated areas must be avoided for at least three weeks. Therefore, as explained above, a relatively short period of pre-surgical, surgical and post-surgical treatment is required.

Bone grafting surgery is appropriate for rejuvenation, reshaping and other similar modifications of body members, including, but not limited to, reshaping or alteration of the shape of the face. As can be seen, bone grafting surgery is relatively easy, simple and without major complications. The surgery may be performed, partially or totally, under local or general anesthesia. Performed surgeries have resulted in rejuvenation of the face almost equivalent to between approximately 15 years to approximately 20 years. The result appears to last longer than face lifts or collagen injections. Another advantage is that due to the presence of hydroxylapatite, this new bone graft mixture used in the bone graft surgical site is firm and stable, and it is anticipated that the new bone graft mixture will remain in place intact for at least approximately 15 years to approximately 20 years. In addition, as described above, the chemicals and medical devices which are needed for performance of bone grafting are relatively simple and inexpensive, thus, making bone grafting a relatively economical method. Meanwhile, even though it is anticipated to yield such long-lasting results, if for any reason the patient is dissatisfied with final results of the surgery, bone graft may be removed at any time after surgery, thus making the final results reversible.

A similar method of surgery can be performed for rejuvenating or reshaping any other body member or to prevent bone loss in body members. The method of surgery may become more popular for facial areas since human beings, in general, are more concerned with appearance of their face, particularly as they pass a certain age and bones start to deteriorate. However, a similar method of surgery can be carried out for other body members which may need rejuvenation or reshaping or a combination of rejuvenation and reshaping. Examples are the hands and the legs and all sections of the legs and of the hands. Basically, if this method of surgery grows and becomes popular, any bone structure of any body member may be reshaped or restructured.

Several surgeries have been performed using bone grafting. No major complications or problems have resulted from said surgeries. Results of two such surgeries are described in detail.

EXAMPLE 1

A 45-year old, French Canadian female patient had a consultation for premature face wrinkles and face rejuvenation on Apr. 18, 1994. Radiographic examinations, cephalometric scans and other clinical examinations showed:

1. Premature bone loss in the cheek areas, nasal triangles and upper maxillar bones;
2. Edentulous maxillae and very severe atrophies in upper alveolar ridges, specifically edentulous mandibles in left and right molar areas;
3. Reduction in SNA ("Sella Nasion Point A" shown by cephalometric analyses); and
4. Wrinkles around nose, upper lip and eyelids and lipid accumulation in double chin area (shown by soft tissue examinations), making the patient appear like a 60-year old woman.

The diagnoses and results of the radiographic and clinical examinations was studied in detail and a solution was proposed to the patient:

1. Performance of an osteological operation (Lefort I Ostéotomie) in the alveolar ridges;
2. Performance of bone grafts in the left side and in the right side of the maxillar bones at least to a degree to advance a minimum of approximately 12 mm in the left side and a minimum of approximately 10 mm in the right side;
3. Treating blepharoplasts in the right side and in the left side;
4. Performance of a "liposuction" in sub-mandibular areas; and
5. Performance of clinical studies by injecting liquid in soft tissues (the patient refused said clinical studies and desired to undergo final surgery as soon as possible), provision of pre-surgical examinations and preparations for examination (e.g. two units of patient blood were prepared by Red Cross and were reserved for the date of surgery).

On Sep. 15, 1994, the patient underwent surgery under general anesthesia. A general summary of the surgery follows:

1. Performance of osteological operation (Lefort I Ostéotomie) and rigid fixation by micro-plate and a number of screws;
2. Mixing of approximately 15 cc of freeze dry demineralized cortical powder bone graft from Donor Network of Arizona with 7 cc of H.A. in 25 cc of normal saline;
3. Preparation of sub-periosteal tunnels in the right side and in the left side and expanding said sub-periosteal tunnels as far as possible in the nasal triangle, in the cheek areas and in sub-orbital areas;
4. Before transporting the bone mixture to desired spots, removing extra normal saline, adding 15 cc of fresh blood of patient and mixing said fresh blood with the mixture of bone graft and H.A.;
5. Closing the tissues by chromic suture;
6. Performance of bilateral blepharoplasts and "liposuction" in sub-mandibular areas by the plastic surgeon;
7. Provision of pre-operative and post-operative antibiotherapy and corticosteroids to the patient; and
8. Provision of post-operative examination and verification on a weekly basis.

EXAMPLE 2

A French Canadian female patient of 53 years old had a consultation on Mar. 3, 1994, for rejuvenation of the face. In that time, the diagnosis indicated:

1. A very serious bone loss in nasal triangles and cheek areas;
2. Presence of wrinkles around the upper lips and the lower lips;
3. Presence of wrinkles around the nose;
4. Indication of a reduction in SNA by a cephalometric analysis; and
5. Deviation of the nose and the nasal septum.

The patient had already had a consultation with a plastic surgeon for treatment of nasal problems. The Applicant offered to the patient the injection of physiological liquid for case study and calculation of bone graft volume as described in the present invention. Patient refused case study and wanted to undergo surgery immediately. The following steps were taken:

1. Preoperative preparation and photography and antibiotherapy were performed.
2. Under conditions of general anesthesia, a rhinoplastic surgery and a septoplastic surgery were carried out by the plastic surgeon on Oct. 17, 1994.
3. After the nasal surgeries, a number of incisions of few millimeters thickness was made in oral epithelium or mucosa, and a subperiosteal tunnel was made in each side of the oral mucosa in the upper jaw. The tunnel was then expanded very gently in the desired areas. About thirty minutes before surgery, a mixture of bone graft was prepared using 10 cc of cortical powder, demineralized bone, 4 cc of hydroxylapatite and 15 cc of normal saline. Before transportation of bone graft, all extra normal saline was removed by suction and a few milliliters of fresh blood of the patient were added to the mixture. The mixture was transported in the areas and the scar was closed. The bone graft was modified by fingers while pressing on patient's outside skin.
4. Post operative advice was given to the patient and weekly visits and control were followed. Three months later, the patient was very happy with her face, but a small nasal surgery was needed to correct the deviation of the nasal septum.

Certain objects are set forth above and made apparent from the foregoing description to describe a certain method of performing said surgery. However, since certain changes may be made in the above method without departing from the scope of the invention, it is intended that all matters contained in the foregoing method shall be interpreted as illustrative only of the principles of the invention and not in a limiting sense. With respect to the above description then, it is to be realized that the optimum dimensional relationships for the parts of the invention, to include variations in size, materials, shape, form and manner of operation, assembly and use, are deemed readily apparent and obvious to one skilled in the art, and all equivalent relationships to those described in the specification are intended to be encompassed by the present invention.

Further, since numerous modifications and changes will readily occur to those skilled in the art, it is not desired to limit the invention to the exact method shown and described, and accordingly, all suitable modifications and equivalents may be resorted to, falling within the scope of the invention. It is also to be understood that the following claims are intended to cover all of the generic and specific features of the invention herein described, and all statements of the scope of the invention which, as a matter of language, might be said to fall therebetween.

What is claimed as invention is:

1. A new method of surgery for rejuvenating or reshaping a body member, said method comprising:
   (a) gradually injecting an amount of physiological serum, including local anesthesia, in a designated site of the body member;
   (b) when a desired shape of the body member is achieved, photographing the body member and determining the injected amount of physiological serum which is equivalent to a quantity of bone graft mixture required for surgery, said bone graft mixture being a mixture of bone graft and hydroxylapatite;
   (c) before injection, combining said bone graft mixture with normal saline to form a paste-like bone graft mixture;
   (d) making a number of incisions and, from said number of incisions, making a tunnel to the designated site for reaching the designated site of the body member and for injecting the bone graft mixture;

(e) transporting with an instrument or injecting with a special syringe the paste-like bone graft mixture to the designated site;

(f) before transporting or injecting the paste-like bone graft mixture to the designated site, removing any extra normal saline from the paste-like bone graft mixture;

(g) combining the bone graft mixture with few milliliters of fresh venous blood from the patient and injecting said bone graft mixture combined with fresh blood at the designated site; and (h) compacting the bone graft mixture gently in the designated site and closing the number of incisions by appropriate surgical sutures, while shaping the body member digitally by pressing on patient's outside skin until the desired shape is achieved.

2. The new method of surgery of claim 1, wherein body member upon which the surgery is performed is the face or any body member which is part of, attached to or proximate to the face.

3. The new method of surgery of claim 1, wherein an injected side of the body member, comprising left side of the face, is compared with an opposite non-injected side of the same body member, comprising right side of the face, and the physiological serum is injected until the desired shape of the injected side is obtained while comparing the injected side with the non-injected side of said body member.

4. The new method of surgery of claim 1, wherein said body member which is treated comprises a bone structure that is reshaped until a desired shape of the body member is obtained.

5. The new method of surgery of claim 1, wherein the bone graft mixture comprises:

(a) a concentration ranging from approximately 60 percent to approximately 80 percent by volume bone graft, said bone graft including, but not limited to, freeze-dried, cortical bone powder derived from human or animal sources; and (b) a concentration ranging from approximately 20 percent to approximately 40 percent by volume hydroxylapatite.

6. The new method of surgery of claim 1, wherein a plaster sculpture of the body member, comprising the face, is prepared by taking an impression with alginate or other similar materials, wax is added on the sculpture to achieve the desired shape, and calculations of the needed amount of bone graft mixture are made according to the amount of wax used.

7. The new method of surgery of claim 1, wherein before the performance of bone grafting surgery upon a large portion of the face, corticosteroids are administered, pre-operatiorily and post-operatorily.

8. The new method of surgery of claim 1, wherein the bone graft mixture has to be prepared a minimum of 30 minutes prior to injection, and then combined with normal saline which has a volume equal to or more than the volume of the bone graft mixture.

9. The new method of surgery of claim 1, wherein:

(a) a number of oral mucosa incisions is made for body parts comprising lower jaw or maxilla and molar and nasal areas, and (b) a tunnel, including but not limited to a sub-periosteal tunnel, is gently dissected to the designated site, while taking special care to prevent any damages to nerves, including but not limited to mandibular and sub-orbital nerves, and assuring that no perforation occurs in the designated site of the bone graft mixture.

10. The new method of surgery of claim 1, wherein for performing a surgery on frontal and temporal parts, a number of small incisions are made in external ends of eyebrows or in hair line, said number of incisions being from skin to periosteum, paying attention to supraorbital nerves.

11. The new method of surgery of claim 1, wherein the surgery is performed, partially or totally, under local or general anesthesia.

12. The new method of surgery of claim 1, wherein the surgery provides a facial rejuvenation method by using bone grafting, rather than by facial lifting.

13. The new method of surgery of claim 1, wherein the bone graft mixture acts as a substitute for an amount of lost bone in the body member, said body member comprising nasal bones and cheek bones of the face, upon which the surgery is performed.

14. The new method of surgery of claim 1, wherein the surgery reshapes the body member, comprising the face, depending upon the patient's needs and desires and wherein, before performance of the surgery, the patient is provided, before the surgery, with a picture of the structure and shape of the body member after rejuvenating or reshaping has been successfully completed.

15. A new method of surgery for rejuvenating or reshaping a body member and for subsequent evaluation, said method comprising:

gradually injecting an amount of physiological serum, including local anesthesia, in a designated site of the body member;

when a desired shape of the body member is achieved, photographing the body member and determining the injected amount of physiological serum which is equivalent to a quantity of bone graft mixture required for surgery, said bone graft mixture being a mixture of bone graft and hydroxylapatite;

before injection, combining said bone graft mixture with normal saline to form a paste-like bone graft mixture;

making a number of incisions and, from said number of incisions, making a tunnel to the designated site for reaching the designated site of the body member and for injecting the bone graft mixture;

transporting with an instrument or injecting with a special syringe the paste-like bone graft mixture to the designated site;

before transporting or injecting the paste-like bone graft mixture to the designated site, removing any extra normal saline from the paste like bone graft mixture;

combining the bone graft mixture with few milliliters of fresh venous blood from the patient and injecting said bone graft mixture combined with fresh blood at the designated site;

compacting the bone graft mixture gently in the designated site and closing the number of incisions by appropriate surgical sutures, while shaping the body member digitally by pressing on patient's outside skin until the desired shape is achieved; and evaluation of the bone graft surgery, wherein an amount of the bone graft mixture is removed making the final results reversible.

16. A new method of surgery for rejuvenating and reshaping a body member, said method comprising:

gradually injecting an amount of physiological serum, including local anesthesia, in a designated site of the body member;

when a desired shape of the body member is achieved, photographing the body member and determining the injected amount of physiological serum which is equivalent to a quantity of bone graft mixture required for surgery, said bone graft mixture being a mixture of bone graft and hydroxylapatite;

before injection, combining said bone graft mixture with normal saline to form a paste-like bone graft mixture;

making a number of incisions and, from said number of incisions, making a tunnel to the designated site for reaching the designated site of the body member and for injecting the bone graft mixture;

transporting with an instrument or injecting with a special syringe the paste-like bone graft mixture to the designated site;

before transporting or injecting the paste-like bone graft mixture to the designated site, removing any extra normal saline from the paste-like bone graft mixture;

combining the bone graft mixture with few milliliters of fresh venous blood from the patient and injecting said bone graft mixture combined with fresh blood at the designated site; and compacting the bone graft mixture gently in the designated site and closing the number of incisions by appropriate surgical sutures, while shaping the body member digitally by pressing on patient's outside skin until the desired shape is achieved.

* * * * *